(12) United States Patent
O'Rear et al.

(10) Patent No.: US 7,404,888 B2
(45) Date of Patent: Jul. 29, 2008

(54) REDUCING METAL CORROSION OF HYDROCARBONS USING ACIDIC FISCHER-TROPSCH PRODUCTS

(75) Inventors: Dennis J. O'Rear, Petaluma, CA (US); Greg Hemighaus, Richmond, CA (US); Gunther H. Dieckmann, Walnut Creek, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 677 days.

(21) Appl. No.: 10/887,109

(22) Filed: Jul. 7, 2004

(65) Prior Publication Data

US 2006/0009663 A1 Jan. 12, 2006

(51) Int. Cl.
*C10L 1/16* (2006.01)
*C10L 1/04* (2006.01)

(52) U.S. Cl. .............................. 208/17; 208/15; 208/19; 585/9; 585/13

(58) Field of Classification Search ........................ None
See application file for complete search history.

(56) References Cited

U.S. PATENT DOCUMENTS

| 2,523,248 | A | 9/1950 | Heinze et al. |
| 5,689,031 | A | 11/1997 | Berlowitz et al. |
| 5,766,274 | A | 6/1998 | Wittenbrink et al. |
| 6,274,029 | B1 | 8/2001 | Wittenbrink et al. |
| 6,296,757 | B1 | 10/2001 | Wittenbrink et al. |
| 6,607,568 | B2 | 8/2003 | Wittenbrink et al. |
| 6,872,752 | B2 * | 3/2005 | O'Rear et al. ............... 518/700 |
| 6,933,323 | B2 * | 8/2005 | O'Rear et al. ............... 518/700 |
| 2006/0283778 | A1 * | 12/2006 | Dupain et al. ............... 208/134 |

FOREIGN PATENT DOCUMENTS

| GB | 0 672 319 | 5/1952 |
| JP | 3 635 140 | 4/2005 |

OTHER PUBLICATIONS

P.P. Shah et al., Fischer-Tropsch Wax Characterization and Upgrading Final Report, United States Department of Energy Under Contract No. DE-AC22-85PC80017 (DE88014638), Jun. 6, 1988, UOP Inc. and Allied-Signal Engineered Materials Research Center.

* cited by examiner

*Primary Examiner*—Tam M Nguyen
(74) *Attorney, Agent, or Firm*—A. Stephen Zavell; James W. Ambrosius

(57) ABSTRACT

A process for reducing the metal corrosion of a hydrocarbonaceous liquid which causes corrosion as measured by NACE Standard TM0172-2001, said process comprising blending with the hydrocarbonaceous liquid at least 0.1 weight percent of an acidic Fischer-Tropsch product in sufficient proportion to produce a hydrocarbonaceous blend displaying reduced metal corrosion as measured by NACE Standard TM0172-2001 when compared to the hydrocarbonaceous liquid and a hydrocarbonaceous blend prepared by the process.

16 Claims, No Drawings

REDUCING METAL CORROSION OF HYDROCARBONS USING ACIDIC FISCHER-TROPSCH PRODUCTS

FIELD OF THE INVENTION

The present invention relates to a method for reducing metal corrosion associated with hydrocarbonaceous liquids by blending into the hydrocarbonaceous liquid an acidic Fischer-Tropsch product.

BACKGROUND OF THE INVENTION

Hydrocarbonaceous liquids are known to induce corrosion in metals with which they have contact during the various phases of production, transport, and use. For example, during transportation via a pipeline, air and water contaminants present in the hydrocarbonaceous liquid can cause corrosion where they contact the interior surface of the pipe. In this situation, the. corrosion appears to be primarily due to the action of water and air on the steel and is not due to the action of the hydrocarbon. While the hydrocarbonaceous liquid itself is not believed to take part in the corrosion, certain hydrocarbonaceous products may actually inhibit corrosion as a result of traces of polar compounds present in the hydrocarbonaceous product. Thus, hydrocarbonaceous liquids free of polar compounds can lead to corrosion problems in pipelines. Consequently, certain pipeline operators have established a minimum corrosion standard for hydrocarbonaceous liquids transported by their pipelines. A widely used test method is NACE Standard TM0172-2001 which in this disclosure may be conveniently described as "NACE". The NACE test involves exposing a rotating steel test specimen to the hydrocarbon, distilled water, and air. Following the contact period, the steel strip is examined for corrosion, and a rating from A to E is assigned based upon the percent of the surface corroded. Generally, a NACE value of B+ or better is required for transportation via pipeline.

Hydrocarbonaceous liquids having a NACE value of B or less usually will require the addition of a corrosion inhibitor to raise the NACE value to an acceptable level. Various corrosion inhibitors are commercially available and well known to those skilled in the art. Although the compositions of these additives are proprietary, typically, they will contain long chain carboxylic acids, alkyenylsuccinic acids, or their amine salts. It is speculated that the acid function attaches to the metal surface and the long pendent portion of the molecule acts as a protective surface against corrosion. These additives are expensive, and it would be desirable to reduce or eliminate their use.

The present invention uses an acidic Fischer-Tropsch product as a corrosion inhibitor for use with hydrocarbonaceous liquids. It has been found that the NACE value may be improved for hydrocarbonaceous liquids by blending in as little as 0.1 weight percent of an acidic liquid Fischer-Tropsch product. For example, it has been found that by blending in an acidic Fischer-Tropsch product as described in this disclosure hydrocarbonaceous liquids having a NACE value of C may achieve a NACE value of B+ or better without the addition of conventional corrosion inhibitors. At the same time, in order to control corrosion in the absence of air and water during the distillation, storage, and other processing operations, it is preferred that the acid number of the hydrocarbonaceous liquid as measured by ASTM D664 not exceed 1.5 mg KOH/gm. Even more preferably, the acid number should not exceed 0.5 mg KOH/gm as measured by ASTM D664.

The "hydrocarbonaceous liquid" referred to in this disclosure may be either petroleum derived or derived from a synthetic process, such as a Fischer-Tropsch synthesis. Liquid hydrocarbons within the scope of this invention include, but are not necessarily limited to, crude oil; base oil; liquid hydrocarbonaceous fuels, such as, for example, motor gasoline, kerosene, naphtha, diesel, fuel oil, aviation kerosene, military DFM; various hydrocarbon feedstock or product blending components, such as, for example, FCC gasoline, iso-octane, reformate, hydrotreated straight run naphtha, hydrotreated mid-distillates; and the like.

As used in this disclosure, the word "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the composition. The phrase "consisting of" or "consists of" is intended as a transition meaning the exclusion of all but the recited elements with the exception of only minor traces of impurities.

SUMMARY OF THE INVENTION

The present invention is directed to a process for reducing the metal corrosion of a hydrocarbonaceous liquid which causes corrosion as measured by NACE Standard TM072-2001, said process comprising blending with the hydrocarbonaceous liquid at least 0.1 weight percent of an acidic Fischer-Tropsch product in sufficient proportion to produce a hydrocarbonaceous blend displaying reduced metal corrosion as measured by NACE Standard TM0172-2001 when compared to the hydrocarbonaceous liquid. In carrying out the present invention, it is preferred that the acidic Fischer-Tropsch product have an acid number of 0.1 mg KOH/gm or greater as determined by analytical method ASTM D664 or its equivalent. Even more preferably, the acid number of the acidic Fischer-Tropsch product will be 0.5 mg KOH/gm or greater as determined by analytical method ASTM D664 or its equivalent.

The present invention is further directed to a hydrocarbonaceous blend having a NACE Standard TM0172-2001 value of B+ or better and an acid number of 1.5 mg KOH/gm or less as measured by ASTM D664, said blend comprising (a) a hydrocarbonaceous liquid having a NACE Standard TM0172-2001 value of B or less and (b) at least about 0.1 weight percent of a Fischer-Tropsch product having an acid number of at least 0.1 mg KOH/gm as measured by ASTM D664. Preferably, the hydrocarbonaceous blend will have an acid number of 0.5 mg KOH/gm or less as measured by analytical method ASTM D664 or its equivalent. Preferably, the Fischer-Tropsch product will comprise between about 1.0 weight percent and about 10.0 weight percent of the hydrocarbonaceous blend.

As used herein, an equivalent analytical method to ASTM D664 refers to any analytical method which gives substantially the same results as the standard method.

DETAILED DESCRIPTION OF THE INVENTION

The NACE Standard TM0172-2001 test method is a standard test used in the industry for evaluating corrosion on metal surfaces. NACE values are a widely used method by pipeline operators to evaluate the corrosive properties of hydrocarbonaceous liquids transported by their pipelines. Generally, a hydrocarbonaceous liquid is required to meet or exceed a minimum NACE rating of B+ to be transported through a pipeline. Hydrocarbons failing to meet the minimum standard must be blended with sufficient corrosion inhibitor to achieve a passing rating. An exception to this requirement is aviation kerosene due to a prohibition of the presence of additives in commercial jet fuel.

Many hydrocarbonaceous liquids contain natural anti-corrosion compounds which probably operate in a similar manner to commercially available corrosion inhibitors, that is, they tend to adhere to the metal surface and protect it from the action of water and air. Unfortunately, refining tends to destroy these native anti-corrosion compounds. Thus, the more highly refined the hydrocarbonaceous fuel, the poorer the NACE rating may be and the greater the amount of corrosion inhibitor required to achieve the minimum standard. As most countries move toward low emission fuels, the hydrocarbonaceous liquids that comprise these fuels, due to increased refining, tend to contain reduced native anti-corrosion compounds. Consequently, the demand for corrosion inhibitors is expected to increase. While corrosion problems are most pronounced in refined products, they can also be present during the transportation of crude oil. The present invention is directed to the discovery that certain products recovered from the Fischer-Tropsch synthesis reaction are able to act as corrosion inhibitors when blended with hydrocarbonaceous liquids.

Fischer-Tropsch Synthesis

During Fischer-Tropsch synthesis, liquid and gaseous hydrocarbons are formed by contacting a synthesis gas (syngas) comprising a mixture of hydrogen and carbon monoxide with a Fischer-Tropsch catalyst under suitable temperature and pressure reactive conditions. The Fischer-Tropsch reaction is typically conducted at temperatures of from about 300 degrees F to about 700 degrees F. (about 150 degrees C. to about 370 degrees C.), preferably from about 400 degrees F. to about 550 degrees F. (about 205 degrees C. to about 288 degrees C.); pressures of from about 10 to about 600 psia (0.7 to 41 bars), preferably 30 to 300 psia (2 to 21 bars); and catalyst space velocities of from about 100 to about 10,000 cc/g/hr., preferably 300 to 3,000 cc/g/hr.

The reaction can be conducted in a variety of reactor types, such as, for example, fixed bed reactors containing one or more catalyst beds, slurry reactors, fluidized bed reactors, or a combination of different types of reactors. Such reaction processes and reactors are well known and documented in the literature. The slurry Fischer-Tropsch process, which is preferred in the production of the acidic Fischer-Tropsch products used in the practice of the invention, utilizes superior heat (and mass) transfer characteristics for the strongly exothermic synthesis reaction and is able to produce relatively high molecular weight, paraffinic hydrocarbons when using a cobalt catalyst. In the slurry process, a syngas comprising a mixture of hydrogen and carbon monoxide is bubbled up as a third phase through a slurry which comprises a particulate Fischer-Tropsch type hydrocarbon synthesis catalyst dispersed and suspended in a slurry liquid comprising hydrocarbon products of the synthesis reaction which are liquid under the reaction conditions. The mole ratio of the hydrogen to the carbon monoxide may broadly range from about 0.5 to about 4, but is more typically within the range of from about 0.7 to about 2.75, and preferably from about 0.7 to about 2.5. A particularly preferred Fischer-Tropsch process is taught in European Patent Application No. 0609079, also completely incorporated herein by reference for all purposes.

Suitable Fischer-Tropsch catalysts comprise one or more Group VIII catalytic metals such as Fe, Ni, Co, Ru and Re. Acidic Fischer-Tropsch products used in the practice of the invention prepared using cobalt based catalysts are particularly preferred due to their excellent anti-corrosion properties. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Suitable support materials include alumina, silica, magnesia and titania or mixtures thereof. Preferred supports for cobalt containing catalysts comprise titania. Useful catalysts and their preparation are known and illustrated in U.S. Pat. No. 4,568,663, which is intended to be illustrative but non-limiting relative to catalyst selection.

The products from the Fischer-Tropsch synthesis may range from $C_1$ to $C_{200}$-plus hydrocarbons with a majority in the $C_5$ to $C_{100}$-plus range. Fischer-Tropsch products as recovered from the Fischer-Tropsch reactor typically are acidic due to the presence of carboxyl groups in the molecules. In addition, the Fischer-Tropsch products usually contain significant amounts of oxygenates, such as alcohols, and olefins.

The Acidic Fischer-Tropsch Product

The hydrocarbon fraction recovered from the Fischer-Tropsch synthesis reactor used to prepare the acidic Fischer-Tropsch products used as a corrosion inhibitor is usually prepared from the condensate fraction, that is, that fraction of the Fischer-Tropsch products which boils between ambient temperature and about 700 degrees F. The condensate fraction is a liquid at ambient temperature and contains hydrocarbons boiling within the range of naphtha and diesel. Preferably, the acidic Fischer-Tropsch product should have a pour point below 20 degrees C. If the acidic Fischer-Tropsch product is derived from the condensate fraction, pour point usually will not be a problem. However, if the acidic Fischer-Tropsch fraction is prepared from higher boiling fractions, such as a base oil fraction, it may be necessary to dewax the acidic Fischer-Tropsch product in order to achieve an acceptable pour point. Dewaxing may be achieved either by solvent dewaxing or by catalytic hydroisomerization; however, catalytic hydroisomerization, if used, must be carried out in such a way as to not completely destroy the desirable acid functions.

The acidic Fischer-Tropsch product preferably will have an acid number of 0.1 mg KOH/gm or greater when measured by analytical method ASTM D664 or its equivalent. Even more preferably, the acidic Fischer-Tropsch product will have an acid number of 0.5 mg KOH/gm or greater when measured by analytical method ASTM D664 or its equivalent. However, in order to control corrosion, an acid number in excess of about 1.5 mg KOH/gm may be undesirable if the acidic Fischer-Tropsch product will be subject to certain downstream refinery operations or storage. Due to the presence of various contaminants, such as oxygenates and dissolved metals, in the Fischer-Tropsch products as they are initially recovered from the Fischer-Tropsch synthesis reaction, selective refining of the acidic Fischer-Tropsch product prior to blending may be desirable. Selective refining may also reduce the acid number, i.e., reduce the number of acid groups on the molecules, if so desired. "Selective refining" as used in this disclosure refers to refining processes which are intended to remove contaminants and/or saturate double bounds without reducing the acid number below an acceptable value. Selective refining usually refers to one or more of the processes selected from the group consisting of dehydration, adsorption, hydrotreating, and extraction. Each of these selective refining processes may be used to remove oxygenates, mostly alcohols, and metal contaminants while retaining an acceptable level of the desirable acids.

While the acidic Fischer-Tropsch product may be prepared using various well known Fischer-Tropsch catalysts, typically, a catalyst containing either iron or cobalt as an active metal, cobalt derived products are preferred in the practice of the invention. Without wishing to be bound by theory, it is speculated that the cobalt-derived acidic Fischer-Tropsch products are more effective because of an optimized distribution of acids. Presumably, the cobalt-derived product contains more high molecular acids and fewer low molecular weight acids. As the molecular weight of the acid increases, presumably, the chemistry of the acid shifts from one of promoting corrosion to one of protecting corrosion. The boiling range of the cobalt-derived product is higher than the iron-derived product. Following this theory, the corrosion protection of the acidic Fischer-Tropsch products could be improved by removing the lower molecular weight acids while retaining the higher molecular weight acids. Accordingly, the acidic Fischer-Tropsch product may be separated into a lighter and a heavier fraction, wherein the lighter fraction contains the lower molecular weight acids and the heavier fraction contains the higher molecular weight acids. The lighter fraction which on balance would be expected to promote corrosion may be treated to remove the more corrosive lighter acids by, for example, processes, such as hydrotreating or decarboxylation. The lighter fraction may optionally be blended back into the heavier fraction or directly into the final hydrocarbonaceous blend. Alternatively, the heavier fraction of the acidic Fischer-Tropsch product may be used alone in the blend.

The Hydrocarbonaceous Liquid

The hydrocarbonaceous liquid is typically a fuel, such as, for example, motor gasoline, kerosene, naphtha, diesel, fuel oil, aviation kerosene, military DFM, and the like. However, the hydrocarbonaceous liquid may also be crude oil; base oil; a hydrocarbon feedstock or a blending component, such as, for example, FCC gasoline, iso-octane, reformate, hydrotreated straight run naphtha, hydrotreated mid-distillates; and the like. The hydrocarbonaceous liquid may be petroleum derived or derived from a synthetic reaction, such as Fischer-Tropsch synthesis. The hydrocarbonaceous liquid may also be a mixture of various petroleum derived hydrocarbons and/or synthetic hydrocarbons. Due to the substantial absence of polar compounds, it will generally have a very low acid number, typically less than about 0.1 mg KOH/gm or less as determined by ASTM D664. Since it is often highly refined, it typically will contain minimal oxygenates and contaminating metals. If it has been hydrotreated, it will usually contain low olefins. The hydrocarbonaceous liquid will have an unacceptable NACE value. If the hydrocarbonaceous liquid is being transported by pipeline, its NACE value will usually be B or less prior to treatment by the process of the invention.

The Hydrocarbonaceous Blend

The hydrocarbonaceous blend comprising the hydrocarbonaceous liquid and the acidic Fischer-Tropsch product will have an improved NACE value as compared to the hydrocarbonaceous liquid alone. Preferably, the NACE value will be B+ or better. The hydrocarbonaceous blend will contain at least 0.1 weight percent of the acidic Fischer-Tropsch product, preferably at least about 0.5 weight percent, and most preferably at least about 1.0 weight percent. As explained below, the practical upper limit on the amount of the acidic Fischer-Tropsch product present in the hydrocarbonaceous blend will usually be determined by the acid number of the blend. Generally, the acidic Fischer-Tropsch product will usually comprise no more than about 10 weight percent of the hydrocarbonaceous blend. However, the optimal amount of acidic Fischer-Tropsch product present in the hydrocarbonaceous blend will be determined by such factors as the acid number of the acidic Fischer-Tropsch product, the NACE value of the hydrocarbonaceous liquid being treated, the acid number that will be acceptable for the final blend, and whether additional corrosion inhibitors will be added.

The hydrocarbonaceous blend should not have an acid number which makes the final blend unsuitable for its intended use. Industry standards state that distillate fractions should have an acid number of 1.5 mg KOH/gm or less as determined by ASTM D664 ("Materials Selection for Petroleum Refineries and Gathering Facilities", Richard A. White, NACE International, 1998, Houston, Texas, pages 6-9). Preferably, the hydrocarbonaceous blend will have an acid number of 0.5 mg KOH/gm or less as determined by ASTM D664. The practical lower limit for determining acid number using ASTM D664 is about 0.05 mg KOH/gm. However, blends that exhibit effective corrosion protection can be prepared by adding very small amounts of the acidic Fischer-Tropsch product which result in an acid number well below the level of detection by ASTM D664. For these blends, the acid number may be calculated by a weighted average of the acid numbers of the blend components.

The hydrocarbonaceous blend may also contain conventional corrosion inhibitors in addition to the acidic Fischer-Tropsch product. Therefore, if the addition of the acidic Fischer-Tropsch product to the hydrocarbonaceous blend fails to raise the NACE value to an acceptable level, conventional corrosion inhibitors may be necessary. However, the amount of conventional corrosion inhibitor necessary to achieve an acceptable NACE value will be reduced.

The following examples are intended to further illustrate the invention but are not intended to be a limitation on the scope of the invention.

EXAMPLES

Example 1

Preparation of a Typical Hydrocarbonaceous Liquid

A hydrocarbonaceous liquid representative of a fully refined diesel product was prepared by blending three individual Fischer-Tropsch components having the properties shown in Table 1, below.

TABLE 1

| Property | Component 1 Cold Condensate | Component 2 Hot Condensate | Component 3 Wax |
|---|---|---|---|
| Wt % in blend | 27.8 | 23.1 | 49.1 |
| Gravity, °API | 56.8 | 44.9 | 40.0 |
| Sulfur, ppm | <1 | <1 | |

TABLE 1-continued

| Property | Component 1 Cold Condensate | Component 2 Hot Condensate | Component 3 Wax |
|---|---|---|---|
| Oxygen, ppm by Neut. Act. | 1.58 | 0.65 | |
| Chemical Types, Wt % by GC-MS | | | |
| Paraffins | 38.4 | 62.6 | 85.3 |
| Olefins | 49.5 | 28.2 | 1.6 |
| Alcohols | 11.5 | 7.3 | 9.3 |
| Other Species | 0.5 | 3.9 | 3.8 |
| Distillation*, °F. by wt % | | | |
| 0.5/5 | 80/199 | 73/449 | 521/626 |
| 10/30 | 209/298 | 483/551 | 666/758 |
| 50 | 364 | 625 | 840 |
| 70/90 | 417/485 | 691/791 | 926/1039 |
| 95/99.5 | 518/709 | 872/1074 | 1095/1184 |

*Analytical method ASTM D2887 may be used for distillations up to 1000 degrees F. ASTM D6352 has a broader scope and may be used up to 1292 degrees F.

The blend was prepared by continuously feeding the three components down-flow to a hydroprocessing reactor. The reactor was filled with a catalyst containing alumina, silica, nickel, and tungsten that had been sulfided prior to use. The LHSV was varied between 0.7 and 1.4, the pressure was constant at 1000 psig, and the recycle gas rate was 4000 SCFM. The per-pass conversion was maintained at approximately 80 percent below the recycle cut point (665-710 degrees F.) by adjusting the catalyst temperature.

The product from the hydroprocessing reactor (after separation and recycling of unreacted hydrogen) was continuously distilled to provide a gaseous by-product, a light naphtha, a diesel fuel, and an unconverted fraction. The unconverted fraction was recycled to the hydroprocessing reactor. The temperature of the distillation column was adjusted to maintain the flash and cloud points at their target values of 58 degrees C. flash and −18 degrees C. cloud point.

Diesel fuel was blended from several hours of consistent operation at 1.4 LHSV to provide the representative product, the properties of which are shown in Table 2, below. The product contained no detectible acids as shown by a neutralization number of 0 mg KOH/gm by ASTM D664.

TABLE 2

| Gravity, °API | 52.7 |
|---|---|
| Nitrogen, ppm | 0.24 |
| Sulfur, ppm | <1 |
| Water, ppm by Karl Fisher, ppm | 21.5 |
| Pour Point, °C. | −23 |
| Cloud Point, °C. | −18 |
| Flash Point, °C. | 58 |
| Autoignition Temperature, °F. | 475 |
| Viscosity at 25° C., cSt | 2.564 |
| Viscosity at 40° C., cSt | 1.981 |
| Cetane Number | 74 |
| Aromatics by Supercritical Fluid Chromatography, wt % | <1 |
| Neutralization No. D664 mg KOH/g | 0 |
| Ash Oxide, Wt % | <0.001 |
| Ramsbottom Carbon Residue, wt % | 0.02 |
| Cu Strip Corrosion | 1A |
| Color, ASTM D1500 | 0 |
| GC-MS Analysis | |
| Paraffins, Wt % | 100 |
| Paraffin i/n ratio | 2.1 |

TABLE 2-continued

| Oxygen as oxygenates, ppm | <6 | |
|---|---|---|
| Olefins, Wt % | 0 | |
| Average Carbon Number | 14.4 | |
| Distillation by D-2887 by Wt %, °F. and D-86 by Vol %, °F. | D-2887 | D-86 |
| 0.5/5 | 255/300 | 329/356 |
| 10/20 | 326/368 | 366/393 |
| 30/40 | 406/449 | 419/449 |
| 50 | 487 | 480 |
| 60/70 | 523/562 | 510/539 |
| 80/90 | 600/637 | 567/597 |
| 95/99.5 | 659/705 | 615/630 |

The diesel fuel contained very low levels of polar compounds (aromatics and heteroatoms). The sample was tested in NACE Standard TM0172-2001 and found to have a rating of C which would be unacceptable for transportation by a pipeline.

Example 2

Preparation of Acidic Fischer-Tropsch Products

Two acidic Fischer-Tropsch products were obtained. The first (Condensate A) was prepared by use of an iron catalyst. The second (Condensate B) was prepared by use of a cobalt catalyst. The Fischer-Tropsch process used to prepare both condensates was operated in the slurry phase. Properties of the two acidic Fischer-Tropsch products are shown below in Table 3, below.

TABLE 3

| Condensate Identification | Fe Cond. A | Co Cond. B |
|---|---|---|
| API | 56.7 | 56.6 |
| Oxygen by NAA, wt % | 1.58 | 0.95 |
| Acid Number (D664), mg KOH/g | 3.47 | 0.86 |
| Cu Strip Corrosion | 3a | 1b |
| Sulfur, ppm wt | <1 | <1 |
| Nitrogen, ppm wt | 0.37 | 1.76 |
| ASTM D28 87 Simulated Distillation by wt %, °F. | | |
| 0.5 | 82 | 76 |
| 10 | 235 | 243 |
| 30 | 301 | 339 |
| 50 | 374 | 415 |
| 70 | 418 | 495 |
| 90 | 487 | 569 |
| 95 | 518 | 596 |
| 99.5 | 691 | 662 |
| Iron by ICP, ppm | 0.8 | 2.020 |

Example 3

Preparation of Hydrocarbonaceous Blends

Varying amounts of the acidic Fischer-Tropsch products prepared in Example 2 (Condensates A and B) were blended with the diesel fuel from Example 1. Each hydrocarbonaceous blend was evaluated in the NACE Standard TM0172-2001. The results are shown in Tables 4 and 5, below.

TABLE 4

Blends of Fe-derived acidic Fischer-Tropsch product (A)

| Blend No. | Cond. A wt % | Diesel wt % | Calculated Blend mg KOH/gm acid | NACE Rating |
|---|---|---|---|---|
| 1 | 0 | 100 | 0.0 | C |
| 2 | 0.1 | 99.9 | 0.003 | B |
| 3 | 1.0 | 99.0 | 0.03 | B |
| 4 | 5.0 | 95.0 | 0.17 | B |
| 5 | 10.0 | 90.0 | 0.35 | A |

TABLE 5

Blends of Co-derived acidic Fischer-Tropsch product (B)

| Blend No. | Cond. B wt % | Diesel wt % | Calculated Blend mg KOH/gm acid | NACE Rating |
|---|---|---|---|---|
| 1 | 0 | 100 | 0.0 | C |
| 6 | 0.1 | 99.9 | 0.0009 | B |
| 7 | 1.0 | 99.0 | 0.009 | B+ |
| 8 | 5.0 | 95.0 | 0.045 | B++ |
| 9 | 10.0 | 90.0 | 0.09 | B++ |

As noted in Example 1, the pure diesel fuel had a failing corrosion rating of C. Adding as little as 0.1 weight percent of either acidic Fischer-Tropsch product increased its rating to B. The calculated acid number for the blend containing the 0.1 weight percent cobalt-derived acidic condensate corresponded to 0.0009 mg KOH/gm. While B is not a passing rating for transportation by pipeline, it would likely result in a reduction in the demand for a corrosion inhibitor additive. A passing rating was obtained by adding between 0.1 and 1.0 weight percent of the cobalt-derived acidic Fischer-Tropsch product, while the iron-derived acidic Fischer-Tropsch product required between 5 and 10 weight percent. For this reason, the cobalt-derived acidic Fischer-Tropsch product is preferred.

Example 4

Selective Refining of Acidic Fischer-Tropsch Product

The cobalt-derived acidic Fischer-Tropsch product (Condensate B) was treated with an alumina dehydration catalyst in a one-inch downflow reactor without added gas or recycle at a temperature of 630 degrees F., 5 LHSV, and a pressure 50 psig. The acidic Fischer-Tropsch product was found to contain 1.1 weight percent oxygenates, indicating that most of the oxygenates originally present in the feed had been reduced to olefins. However, the acid number was 0.67 mg KOH/gm as determined by ASTM D664, indicating that the acid sites had been less affected by the operation.

Example 5

Improvement of NACE Value in Petroleum—Derived Jet Fuel

A commercial jet fuel meeting ASTM D1655 specifications for Jet A was blended in various proportions with the acidic Fischer-Tropsch product prepared in Example 4. The jet fuel had an acid content of less than 0.05 mg KOH/gm (the lower detection limit for ASTM D664) and was assumed to be zero in the calculated blend acidity shown in the table. The results are shown in Table 6, below.

TABLE 6

| Blend No. | FT Product Wt. % | Jet Wt. % | Calculated Blend mg KOH/gm acid | NACE Rating |
|---|---|---|---|---|
| 10 | 0 | 100 | 0.0 | D |
| 11 | 0.1 | 99.9 | 0.0007 | C |
| 12 | 1.0 | 99.0 | 0.007 | B+ |
| 13 | 5.0 | 95.0 | 0.034 | B++ |
| 14 | 10.0 | 90.0 | 0.07 | A |

Note that a passing NACE rating of B+ is obtained from blends of petroleum-derived jet fuel and the selectively refined acidic Fischer-Tropsch product when the blend displays an acid number of 0.007 mg KOH/gm or greater when measured by ASTM D664. This is consistent with the amount of acid (0.009 mg KOH/gm) needed to produce an acceptable blend with the untreated cobalt-derived acidic Fischer-Tropsch product as illustrated in Example 3, Table 5.

What is claimed is:

1. A process for reducing the metal corrosion of a hydrocarbonaceous liquid which causes corrosion as measured by NACE Standard TM0172-2001, said process comprising blending with the hydrocarbonaceous liquid at least 0.1 weight percent of an acidic Fischer-Tropsch product in sufficient proportion to produce a hydrocarbonaceous blend displaying reduced metal corrosion as measured by NACE Standard TM0172-2001 when compared to the hydrocarbonaceous liquid.

2. The process of claim 1 wherein the hydrocarbonaceous liquid is petroleum derived.

3. The process of claim 1 wherein the hydrocarbonaceous liquid is derived from a Fischer-Tropsch synthesis.

4. The process of claim 1 wherein the acidic Fischer-Tropsch product is prepared by a Fischer-Tropsch synthesis reaction using a cobalt based Fischer-Tropsch catalyst.

5. The process of claim 1 wherein the acidic Fischer-Tropsch product is prepared from the condensate fraction of the hydrocarbons recovered from the Fischer-Tropsch process.

6. The process of claim 1 wherein the acidic Fischer-Tropsch product has an acid number 0.1 mg KOH/gm or greater as measured by ASTM D664.

7. The process of claim 6 wherein the acidic Fischer-Tropsch product has an acid number of 0.5 mg KOH/gm or greater as measured by ASTM D664.

8. The process of claim 1 wherein the acidic Fischer-Tropsch product has been selectively refined by means of at least one of the processes selected from the group consisting of dehydration, adsorption, hydrotreating, and extraction prior to blending with the hydrocarbonaceous liquid.

9. The process of claim 1 wherein the hydrocarbonaceous liquid has a NACE Standard TM0172-2001 rating of C or poorer.

10. The process of claim 9 wherein the hydrocarbonaceous blend has a NACE Standard TM0172-2001 rating of B or better.

11. The process of claim 10 wherein the hydrocarbonaceous blend has a NACE Standard TM0172-2001 rating of B+ or better.

12. The process of claim 1 wherein the blend has an acid number of 1.5 mg KOH/gm or less as measured by ASTM D664.

13. The process of claim 1 wherein the blend has an acid number of 0.5 mg KOH/gm or less as measured by ASTM D664.

14. The process of claim 1 wherein the hydrocarbonaceous blend contains at least 0.5 weight percent of the acidic Fischer-Tropsch product.

15. The process of claim 14 wherein the hydrocarbonaceous blend contains at least 1.0 weight percent of the acidic Fischer-Tropsch product.

16. The process of claim 1 further including mixing a corrosion inhibitor into the hydrocarbonaceous blend.

* * * * *